US010694968B2

(12) United States Patent
Deouell et al.

(10) Patent No.: US 10,694,968 B2
(45) Date of Patent: Jun. 30, 2020

(54) CLASSIFYING EEG SIGNALS IN RESPONSE TO VISUAL STIMULUS

(71) Applicants: Yissum Research Development Company of the Hebrew University of Jerusalem Ltd., Jerusalem (IL); B.G. Negev Technologies & Applications Ltd., at Ben-Gurion University, Beer-Sheva (IL)

(72) Inventors: Leon Y. Deouell, Tel-Aviv (IL); Amir B. Geva, Tel-Aviv (IL); Galit Fuhrmann Alpert, Jerusalem (IL); Ran El Manor, Savyon (IL); Shani Shalgi, Hod-HaSharon (IL)

(73) Assignees: Yissum Research Development Company of the Hebrew University of Jerusalem Ltd., Jerusalem (IL); B.G. Negev Technologies & Applications Ltd., at Ben-Gurion University, Beer-Sheva (IL)

( * ) Notice: Subject to any disclaimer, the term of this patent is extended or adjusted under 35 U.S.C. 154(b) by 0 days.

(21) Appl. No.: 14/784,314

(22) PCT Filed: Apr. 13, 2014

(86) PCT No.: PCT/IL2014/050355
§ 371 (c)(1),
(2) Date: Oct. 14, 2015

(87) PCT Pub. No.: WO2014/170897
PCT Pub. Date: Oct. 23, 2014

(65) Prior Publication Data
US 2016/0051163 A1 Feb. 25, 2016

Related U.S. Application Data

(60) Provisional application No. 61/811,784, filed on Apr. 14, 2013.

(51) Int. Cl.
*A61B 5/0484* (2006.01)
*A61B 5/04* (2006.01)
(Continued)

(52) U.S. Cl.
CPC ...... *A61B 5/04842* (2013.01); *A61B 5/04012* (2013.01); *A61B 5/0476* (2013.01);
(Continued)

(58) Field of Classification Search
None
See application file for complete search history.

(56) References Cited

U.S. PATENT DOCUMENTS

| 3,841,309 A * | 10/1974 | Salter | A61B 5/0476 600/544 |
|---|---|---|---|
| 2001/0031925 A1 * | 10/2001 | Mika | A61B 5/0402 600/510 |

(Continued)

FOREIGN PATENT DOCUMENTS

| WO | WO 2006/026548 | 3/2006 |
|---|---|---|
| WO | WO 2014/170897 | 10/2014 |

OTHER PUBLICATIONS

Bigdely-Shamlo et al.; Brain Activity-Based Image Classification From Rapid Serial Visual Presentation; IEEE Transactions on Neural Systems and Rehabilitation Engineering, vol. 16, No. 5, Oct. 2008.*

(Continued)

*Primary Examiner* — Etsub D Berhanu
*Assistant Examiner* — Jay B Shah

(57) ABSTRACT

Systems and method for classifying EEG signals of a human subject generated responsive to a series of images containing target images and non-target images. The EEG signals are in a spatio-temporal representation. The time points are classified independently, using a linear discriminant classifier, to (Continued)

compute spatio-temporal discriminating weights that are used to amplify the spatio-temporal representation, to create a spatially-weighted representation. Principal Component Analysis is used on a temporal domain for dimensionality reduction, separately for each spatial channel of the signals, to create a projection, which is applied to the spatially-weighted representation onto a first plurality of principal components, to create a temporally approximated spatially weighted representation. The temporally approximated spatially weighted representation is classified over the channels, using said linear discriminant classifier, to yield a binary decisions series indicative of each image of the images series as either belonging to said target image or to said non-target image.

12 Claims, 5 Drawing Sheets

(51) Int. Cl.
  *A61B 5/0476* (2006.01)
  *A61B 5/00* (2006.01)
(52) U.S. Cl.
  CPC .......... *A61B 5/4064* (2013.01); *A61B 5/7203* (2013.01); *A61B 2576/026* (2013.01)

(56) References Cited

U.S. PATENT DOCUMENTS

| | | | | | |
|---|---|---|---|---|---|
| 2004/0197016 | A1* | 10/2004 | Littlefield | ............ | G01N 29/225 382/128 |
| 2009/0137924 | A1* | 5/2009 | Kapoor | ............ | A61B 5/04012 600/545 |
| 2012/0089552 | A1* | 4/2012 | Chang | ............ | G06F 17/30817 706/52 |

OTHER PUBLICATIONS

Lan et al.; A Comparison of Different Dimensionality Reduction and Feature Selection Methods for Single Trial ERP Detection; Conf Proc IEEE Eng Med Biol Soc. 2010.*
Alpert et al.—Spatio-Temporal Representations of Rapid Visual Target Detection: A Single Trial EEG Classification Algorithm, IEEE Transactions on Biomedical Engineering 2013 (Year: 2013).*
International Preliminary Report on Patentability dated Oct. 29, 2015 From the International Bureau of WIPO Re. Application No. PCT/IL2014/050355.
International Search Report and the Written Opinion dated Jun. 25, 2015 From the International Searching Authority Re. Application No. PCT/IL2014/050355.
Bashashti et al. "A Survey of Signal Processing Algorithms in Brain-Computer Interfaces Based on Electrical Brain Signals", Journal of Neural Engineering, XP020123730, 4(2): R32-R57, Mar. 27, 2007. Abstract, Tables 3-7.
Fuhrmann Alpert et al. "Identifying Brain Activity Related to Visual Target Detection in Single Trial EEG Data", Abstract From the Israeli Society for Neuroscience Meeting, Journal of Molecular Neuroscience, 45(1 Suppl.): 1-137, Nov. 2011.
Fuhrmann Alpert et al. "Identifying Brain Activity Related to Visual Target Detection in Single Trial EEG Data", Israeli Society for Neuroscience Meeting, Elat, Israel, Poster, Dec. 2010.
Fuhrmann Alpert et al. "Object Categorization of Visually Presented Images Occurs Early in Time and Space: Single Trial EEG Classification Analysis", Poster, Mallorca, Spain, Sep. 2011.
Majumdar "Human Scalp EEG Processing: Various Soft Computing Approaches", Applied Soft Computing, XP028303696, 11(8): 4433-4447, Available Online Jul. 30, 2011. Abstract, Sections 1-3, 7.
Parra et al. "Recipes for the Linear Analysis of EEG", NeuroImage, XP005109825, 28(2): 326-341, Nov. 1, 2005. Abstract, p. 326, col. 2, Para 2-p. 327, col. 1, Para 3, p. 327, col. 2, p. 330, col. 1, Para 4-p. 333, col. 1, Para 2, p. 334, col. 1, Para 3-p. 335, col. 1, Para 6, p. 337, col. 1, Para 2, 3, Figs.3, 4.
Office Action dated May 26, 2019 From the Israel Patent Office Re. Application No. 242073 and Its Translation Into English. (6 Pages).
Office Action dated Feb. 5, 2020 From the Israel Patent Office Re. Application No. 242073 and Its Translation Into English. (5 Pages).
Requisition by the Examiner dated Apr. 14, 2020 From the Innovation, Science and Economic Development Canada, Canadian Intellectual Property Office Re. Application No. 2,909,017.

\* cited by examiner

CLASSIFYING EEG SIGNALS IN RESPONSE TO VISUAL STIMULUS

RELATED APPLICATIONS

This application is a National Phase of PCT Patent Application No. PCT/IL2014/050355 having International filing date of Apr. 13, 2014, which claims the benefit of priority under 35 USC § 119(e) of U.S. Provisional Patent Application No. 61/811,784 filed on Apr. 14, 2013. The contents of the above applications are all incorporated by reference as if fully set forth herein in their entirety.

FIELD OF THE INVENTION

The present invention relates generally to the field of biomedical signal processing and in particular to systems and methods for classifying Electroencephalography signals.

BACKGROUND OF THE INVENTION

Brain Computer Interface applications, developed for both healthy and clinical populations critically depend on decoding brain activity in single trials.

Recent advances in Neuroscience have led to an emerging interest in Brain Computer Interface (BCI) applications for both disabled and healthy populations. These applications critically depend on online decoding of brain activity, in response to single events (trials), as opposed to delineation of the average response frequently studied in basic research. Electroencephalography (EEG), a noninvasive recording technique, is one of the commonly used systems for monitoring brain activity. EEG data is simultaneously collected from a multitude of channels at a high temporal resolution, yielding high dimensional data matrices for the representation of single trial brain activity. In addition to its unsurpassed temporal resolution, EEG is non-invasive, wearable, and more affordable than other neuroimaging techniques, and is thus a prime choice for any type of practical BCI. The two other technologies used for decoding brain activity, namely functional MRI and MEG, require cumbersome, expensive, and non-mobile instrumentation, and although they maintain their position as highly valuable research tools, are unlikely to be useful for routine use of BCIs. Traditionally, EEG data has been averaged over trials to characterize task-related brain responses despite the on-going, task independent "noise" present in single trial data. However, in order to allow flexible real-time feedback or interaction, task-related brain responses need to be identified in single trials, and categorized into the associated brain states. Most classification methods use machine-learning algorithms, to classify single-trial spatio-temporal activity matrices based on statistical properties of those matrices. These methods are based on two main components a feature extraction mechanism for effective dimensionality reduction, and a classification algorithm.

Typical classifiers use a sample data to learn a mapping rule by which other test data can be classified into one of two or more categories. Classifiers can be roughly divided to linear and non-linear methods. Non-linear classifiers, such as Neural Networks, Hidden Markov Model and k-nearest neighbor, can approximate a wide range of functions, allowing discrimination of complex data structures. While non-linear classifiers have the potential to capture complex discriminative functions, their complexity can also cause overfitting and carry heavy computational demands, making them less suitable for real-time applications.

Linear classifiers, on the other hand, are less complex and are thus more robust to data overfitting. Naturally, linear classifiers perform particularly well on data that can be linearly separated. Fisher Linear discriminant (FLD), linear Support Vector Machine (SVM) and Logistic Regression (LR) are popular examples. FLD finds a linear combination of features that maps the data of two classes onto a separable projection axis. The criterion for separation is defined as the ratio of the distance between the classes mean to the variance within the classes. SVM finds a separating hyper-plane that maximizes the margin between the two classes. LR, as its name suggests, projects the data onto a logistic function. All linear classifiers offer fast solution for data discrimination, and are thus most commonly applied in classification algorithms used for real-time BCI applications.

Whether linear or non-linear, most classifiers require a prior stage of feature extraction. Selecting these features has become a crucial issue, as one of the main challenges in deciphering brain activity from single trial data matrices is the high dimensional space in which they are embedded, and the relatively small sample sizes the classifiers can rely on in their learning stage. Feature extraction is in essence a dimensionality reduction procedure mapping the original data onto a lower dimensional space. A successful feature extraction procedure will pull out task-relevant information and attenuate irrelevant information. Some feature extraction approaches use prior knowledge, such as specific frequency-bands relevant to the experiment or brain locations most likely to be involved in the specific classification problem. For instance, the literature has robustly pointed out parietal scalp regions to be involved in target detection paradigms, as a specific target-related response at parietal regions, known as the P300 wave, has been repeatedly observed approximately 300-500 ms post-stimulus. Such prior-knowledge based algorithms, in particular P300 based systems, are commonly used for a variety of BCI applications. In contrast, other methods construct an automatic process to pull out relevant features based on supervised or unsupervised learning from training data sets. Some approaches for automatic feature extraction include Common Spatial Patterns (CSP), autoregressive models (AR) and Principal Component Analysis (PCA). CSP extracts spatial weights to discriminate between two classes, by maximizing the variance of one class while minimizing the variance of the second class. AR instead focuses on temporal, rather than spatial, correlations in a signal that may contain discriminative information. Discriminative AR coefficients can be selected using a linear classifier. Other methods search for spectral features to be used for classification. PCA is used for unsupervised feature extraction, by mapping the data onto a new, uncorrelated space where the axes are ordered by the variance of the projected data samples along the axes, and only those axes reflecting most of the variance are maintained. The result is a new representation of the data that retains maximal information about the original data yet provides effective dimensionality reduction. PCA is used in the current study and is further elaborated in the following sections. Such methodologies of single-trial EEG classification algorithms have been implemented for a variety of BCI applications, using different experimental paradigms. Most commonly, single-trial EEG classification has been used for movement-based and P300 based-applications. Movement tasks, both imaginary and real, have been studied for their potential use with disabled subjects. P300 applications, based on visual or auditory oddball experiments, originally aimed at providing BCI-based communication devices for locked-in patients and can also be used for a variety of applications for healthy individuals. Emotion assessment, for example, attempts to classify emotions to categories (negative, positive and neutral) using a combination of EEG and other physiological signals, offering a potential tool for behavior prediction and monitoring.

An implementing a BCI framework is aimed at, in order to sort large image databases into one of two categories (target images; non-targets). EEG patterns are used as markers for target-image appearance during rapid visual presentation. Subjects are instructed to search for target images (a given category out of five) within a rapid serial visual presentation (RSVP; 10 Hz). In this case, the methodological goal of the classification algorithm is to automatically identify, within a set of event related responses, single trial spatio-temporal brain responses that are associated with the target image detection. In addition to the common challenges faced by single-trial classification algorithms for noisy EEG data, specific challenges are introduced by the RSVP task, due to the fast presentation of stimuli and the ensuing overlap between consecutive event related responses. Some methods have thus been constructed specifically for the RSVP task.

One such method, developed specifically for single-trial classification of RSVP data used spatial Independent Component Analysis (ICA) to extract a set of spatial weights and obtain maximally independent spatial-temporal sources. A parallel ICA step was performed in the frequency domain to learn spectral weights for independent time-frequency components. Principal Component Analysis (PCA) was used separately on the spatial and spectral sources to reduce the dimensionality of the data. Each feature set was classified separately using Fisher linear Discriminants and then combined using naive Bayes fusion (i.e., multiplication of posterior probabilities).

A more general framework was proposed for single trial classification, and was also implemented specifically for the RSVP task. The suggested framework uses a bilinear spatial-temporal projection of event related data on both temporal and spatial axes. These projections can be implemented in many ways. The spatial projection can be implemented, for example, as a linear transformation of EEG scalp recordings into underlying source space or as ICA. The temporal projection can be thought of as a filter. The dual projections are implemented on non-overlapping time windows of the single-trial data matrix, resulting in a scalar representing a score per window. The windows' scores are summed or classified to provide a classification score for the entire single trial. In addition to the choice of projections, this framework can support additional constraints on the structure of the projections matrix. One option is, for example, to learn the optimal time window for each channel separately and then train the spatial terms.

BRIEF SUMMARY OF THE INVENTION

According to some embodiments of the present invention, a method for conduction of single trial classification of EEG signals of a human subject generated responsive to a series of images containing target images and non-target images, the method comprising: obtaining said EEG signals in a spatio-temporal representation comprising time points and respective spatial distribution of said EEG signals; classifying said time points independently, using a linear discriminant classifier, to compute spatio-temporal discriminating weights; using said spatio-temporal discriminating weights to amplify said spatio-temporal representation by said spatio-temporal discriminating weights at tempo-spatial points respectively, to create a spatially-weighted representation; using Principal Component Analysis (PCA) on a temporal domain for dimensionality reduction, separately for each spatial channel of said EEG signals, to create a PCA projection; applying said PCA projection to said spatially-weighted representation onto a first plurality of principal components, to create a temporally approximated spatially weighted representation containing for each spatial channel, PCA coefficients for said plurality of principal temporal projections; and classifying said temporally approximated spatially weighted representation, over said number of channels, using said linear discriminant classifier, to yield a binary decisions series indicative of each image of the images series as either belonging to said target image or to said non-target image. These additional, and/or other aspects and/or advantages of the present invention are set forth in the detailed description which follows.

BRIEF DESCRIPTION OF THE DRAWINGS

For a better understanding of the invention and in order to show how it may be implemented, references are made, purely by way of example, to the accompanying drawings in which like numerals designate corresponding elements or sections. In the accompanying drawings.

DETAILED DESCRIPTION OF THE INVENTION

Figure 1:
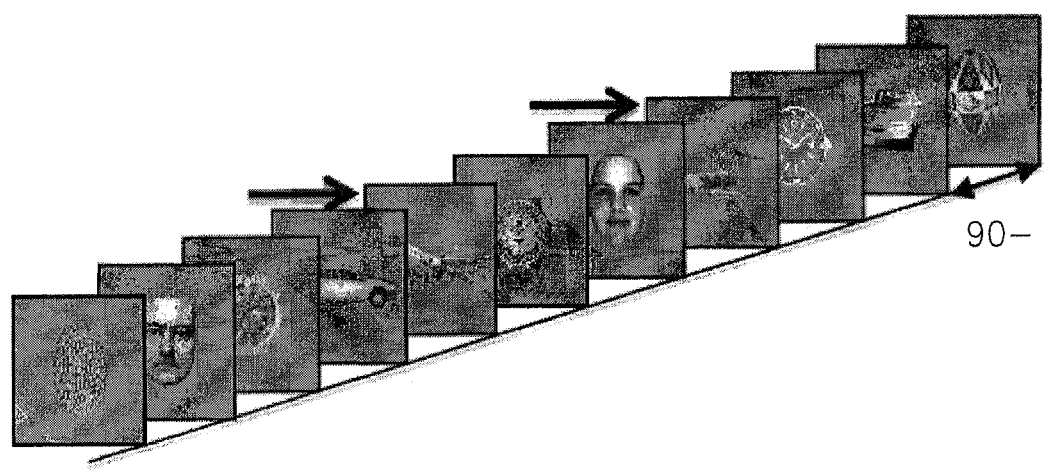
FIG. 1 is a diagram illustrating images presented to a human subject in an experiment carried out in accordance with some embodiments of the present invention.

With specific reference now to the drawings in detail, it is stressed that the particulars shown are for the purpose of example and solely for discussing the preferred embodiments of the present invention, and are presented in the cause of providing what is believed to be the most useful and readily understood description of the principles and conceptual aspects of the invention. In this regard, no attempt is made to show structural details of the invention in more detail than is necessary for a fundamental understanding of the invention. The description taken with the drawings makes apparent to those skilled in the art how the several forms of the invention may be embodied in practice.

Before explaining the embodiments of the invention in detail, it is to be understood that the invention is not limited in its application to the details of construction and the arrangement of the components set forth in the following descriptions or illustrated in the drawings. The invention is applicable to other embodiments or of being practiced or carried out in various ways. Also, it is to be understood that the phraseology and terminology employed herein is for the purpose of description and should not be regarded as limiting.

The present invention, in embodiments thereof, provide an ability to detect distinctive spatiotemporal brain patterns within a set of event related responses.

A novel classification algorithm is provided herein, the Spatially Weighted FLD-PCA (SWFP), which is based on a 2-step linear classification of event-related responses, using Fisher Linear Discriminant (FLD) classifier and principal component analysis (PCA) for dimensionality reduction.

In an experiment conducted, whose details are provided hereinafter, the suggested algorithm was applied to detect target images within a rapid serial visual presentation (RSVP, 10 Hz) of images from five different object categories, based on single trial brain responses. We find a systematic superiority of our classification algorithm in the tested paradigm. Additionally, HDPCA significantly increases classification accuracies compared to the HDCA.

According to some embodiments of the present invention, a method for conducting a single trial classification of EEG signals of a human subject generated responsive to a series of images containing target images and non-target images, is provided herein. The method may include the following stages: obtaining said EEG signals in a spatio-temporal representation comprising time points and respective spatial distribution of said EEG signals; classifying said time points independently, using a linear discriminant classifier, to compute spatio-temporal discriminating weights; using said spatio-temporal discriminating weights to amplify said spatio-temporal representation by said spatio-temporal discriminating weights at tempo-spatial points respectively, to create a spatially-weighted representation; using Principal Component Analysis (PCA) on a temporal domain for dimensionality reduction, separately for each spatial channel of said EEG signals, to create a PCA projection; applying said PCA projection to said spatially-weighted representation onto a first plurality of principal components, to create a temporally approximated spatially weighted representation containing for each spatial channel, PCA coefficients for said plurality of principal temporal projections; and classifying said temporally approximated spatially weighted representation, over said number of channels, using said linear discriminant classifier, to yield a binary decisions series indicative of each image of the images series as either belonging to said target image or to said non-target image.

In the amplification, each time point at each channel in the original matrix is multiplied by the weight of that channel for this time point in the weighting matrix. So for each time point, the channel that contribute more to the classification will be augmented relative to the ones that contribute less to classification which will be suppressed.

According to some embodiments, the spatio-temporal representation comprises a data matrix X whose columns represent time points, each time point being spatial distribution of the EEG signals at time t, wherein the spatio-temporal discriminating weights comprises matrix U, wherein the spatially-weighted representation comprises matrix $X_w$, wherein the PCA projection comprises matrix A, wherein the plurality of principal components comprise first K principal components, wherein the temporally approximated spatially weighted representation comprises matrix $\hat{X}$ of size D×K, wherein D is a number of the EEG spatial channels, and wherein the binary decisions series is represented by $y_n$ such that: $y_n = f(\hat{X}_n)$; $\hat{X}_n = A(U.*\hat{X}^T_n)$, wherein $\hat{X}_n = A X_w$.

According to some embodiments, at least some of the target images are repeated in the image series to increase accuracy of said binary decisions series. Specifically, presenting several repetitions of the same image exemplars improve accuracy, and thus may be important in cases where high accuracy is crucial.

According to some embodiments, the images at the image series are presented to the human subject at a rate of approximately 2-10 Hz. More specifically, the rate is selected so that it can cope with overlapping responses in a rapid series of visual presentation.

According to some embodiments, the target images are related to a visually resembling class, so that a class of "cars" or "planes" may include different images of similar objects.

According to some embodiments, the human subject is provided with a priori knowledge regarding said target images, and wherein said binary decisions series is analyzed based on said a priori knowledge. Alternatively, the human subject lacks any a priori knowledge regarding said target images, and wherein said binary decisions series is analyzed based on said lack of a priori knowledge.

The Experiment

Following below, is a detailed description of an experiment carried out by the inventors. The experiment illustrates embodiments of the present invention and should not be regarded as limiting. In the experiment, human subjects were instructed to count the occurrence of target images of one category out of five (cars, painted eggs, faces, planes, or clock faces) within a rapid serial visual presentation (RSVP). Each image exemplar was presented several times during the experiment. Eye position was monitored at 1000 Hz resolution.

Images were presented in 4 blocks, with a different target category in each block (clock faces were not used as targets). The order of blocks was counterbalanced across subjects. Each block consisted of an RSVP of 6525 images, presented without inter-stimulus intervals every 90-110 ms rates (i.e., ~10 Hz). In each block, 20% of the images were targets, randomly distributed within the block. The subjects' task was to count the occurrences of the target category (e.g. "count the planes"). Presentation was briefly paused every 80-120 trials and the subject was asked to report how many targets appeared in the last run, and thereafter restart the count. This was done to avoid the working memory load of accumulating large numbers. The experimental paradigm is depicted in FIG. 1.

In the experiment, EEG recordings were acquired by an Active 2 system (BioSemi, the Netherlands) using 64 sintered Ag/AgCl electrodes, at a sampling rate of 256 Hz with an online low-pass filter of 51 Hz to prevent aliasing of high frequencies. Seven additional electrodes were placed as follows: two on the mastoid processes, two horizontal EOG channels positioned at the outer canthi of the left and right eyes (HEOGL and HEOGR, respectively), two vertical EOG channels, one below (infraorbital, VEOGI) and one above (supraorbital, VEOGS) the right eye, and a channel on the tip of the nose. All electrodes were referenced to the average of the entire electrode set, excluding the EOG channels. Offline, a bipolar vertical EOG (VEOG) channel was calculated as the difference between VEOGS and VEOGI. Similarly, a bipolar horizontal EOG channel (HEOG) was calculated as the difference between HEOGL and HEOGR. Blinks were removed by rejecting epochs in which the VEOG bipolar channel exceeded ±100 μV. The same criterion was also applied to all other channels to reject occasional recording artifacts and gross eye movements.

A high-pass filter of 0.1 Hz was used offline to remove slow drifts. The data was segmented to one-second event-related segments starting 100 ms prior to and ending 900 ms after the onset of each image presentation, yielding, for each subject, a large channel x time spatio-temporal data matrices for the representation of single trial brain activity. Baseline correction was performed by subtracting the mean activity at 100 ms prior to stimulus onset for each trial and channel independently.

In all cases, single trial data is represented by the spatio-temporal activity matrix X of size D×T, containing raw event-related signals recorded from all EEG channels at all time points, locked to the onset of an image presentation. D is the number of EEG channels, and T is the number of time points.

Due to low signal to noise ratios (SNRs) of EEG data, the standard approach to analyzing event-related responses is to study the mean Event Related Potential (ERP), averaged over repeated trials of the same stimulus condition.

Figure 2:
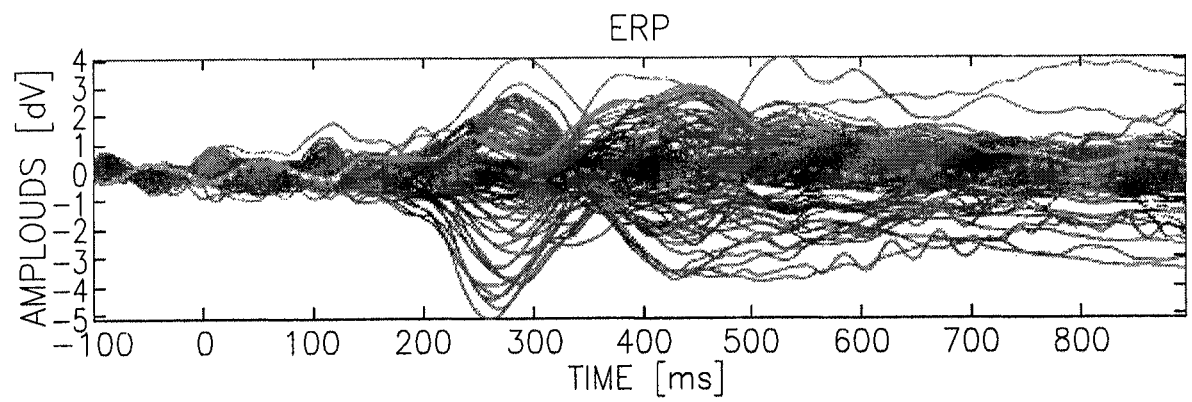
FIGS. 2, 3, 4, 5, 6 and 7 are various graphs and distribution diagrams illustrating the results received and analyzed in the experiment carried out in accordance with some embodiments of the present invention.
Figure 2:
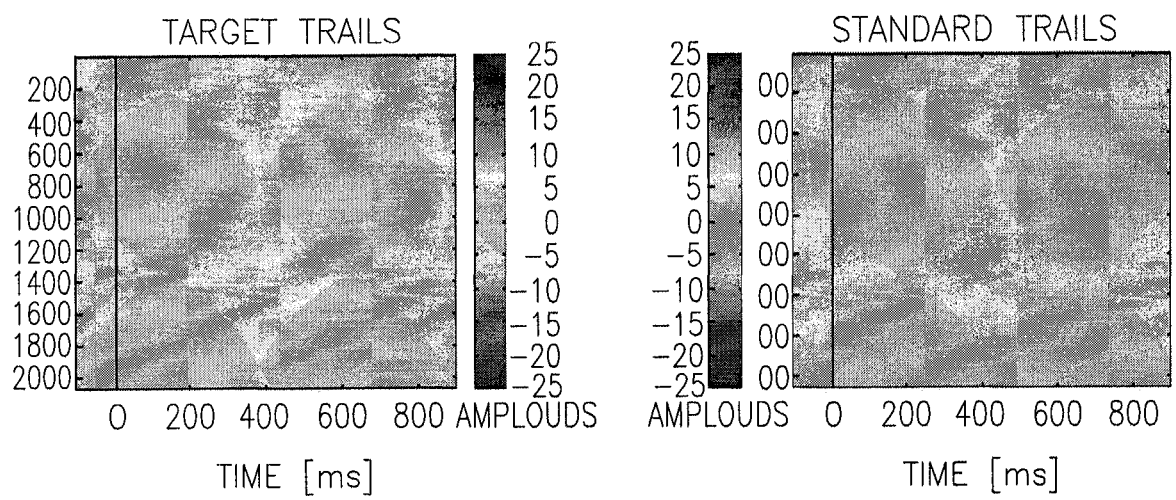
Figure 3:
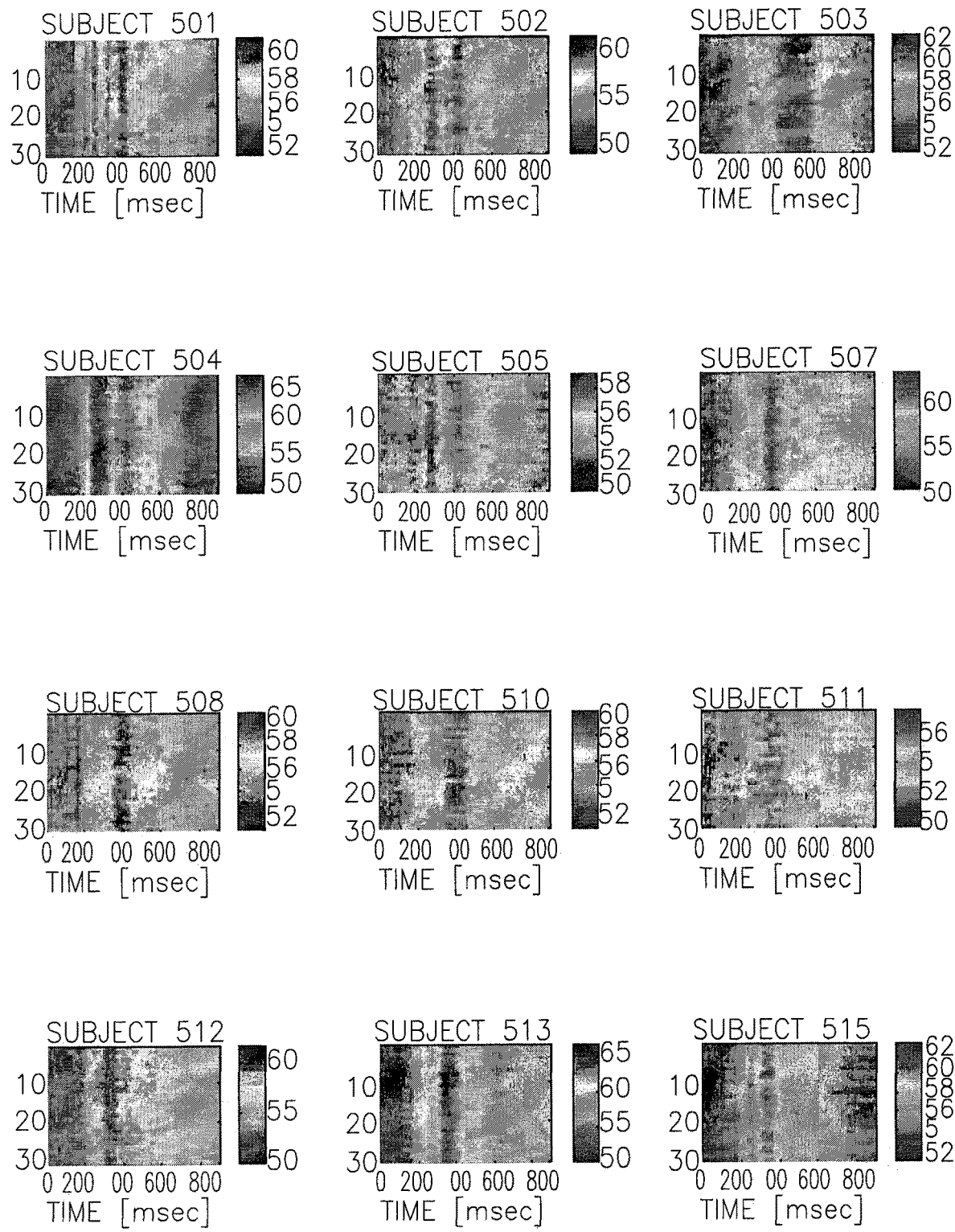

FIG. 2 depicts a 'butterfly plot' of ERPs elicited by the Target (Red) and Standard (blue) ERPs computed for each of the recording channels, collapsed over blocks of the main paradigm (Experiment 1) for a single sample subject. Note that on average, despite the rapid sequence of events and the overlapping responses, the main divergence between Target and Standard ERPs occurs between 300-500 ms post-image FIG. 3 shows the temporal dependence of correct classification for all subjects at each cross validation permutation. Note that at different permutations, temporal dependence may vary to some extent, but there's a high degree of consistency within subject, across cross validation permutations. The specific pattern of temporal dependence of performance varies across subjects however, highlighting the somewhat idiosyncratic yet stable pattern of brain responses that usually escapes notice when grand averages are used.

Figure 4:
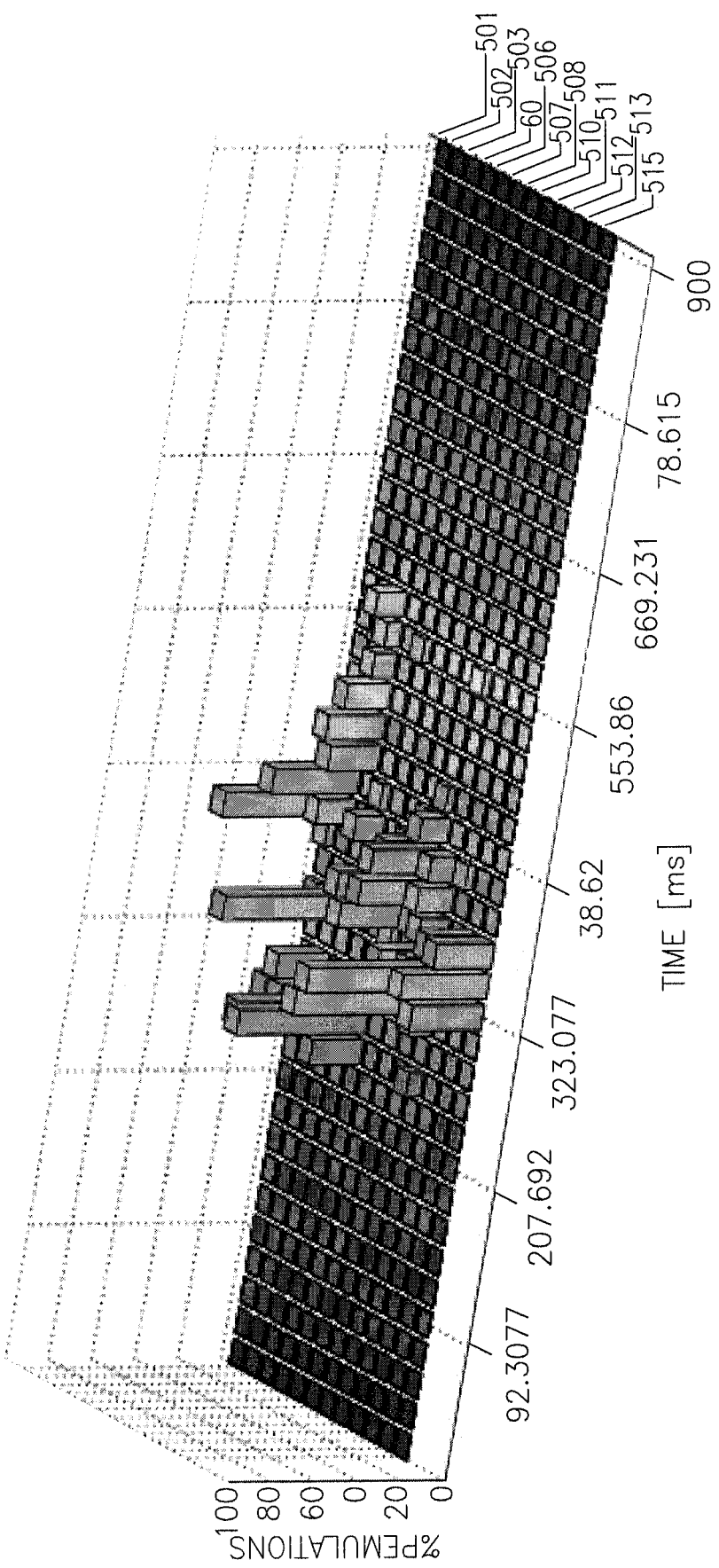

For each cross validation permutation, we defined the most discriminative response latency ($T_{best}$) as the post-stimulus latency at which the highest percent correct classification is achieved. FIG. 4 shows the probability distributions for best latencies, calculated for all cross validation permutations. Evidently, different subjects have different preferred latencies for Target/Standard discrimination, but almost all are roughly around 300-500 ms post-image presentation.

Figure 5:
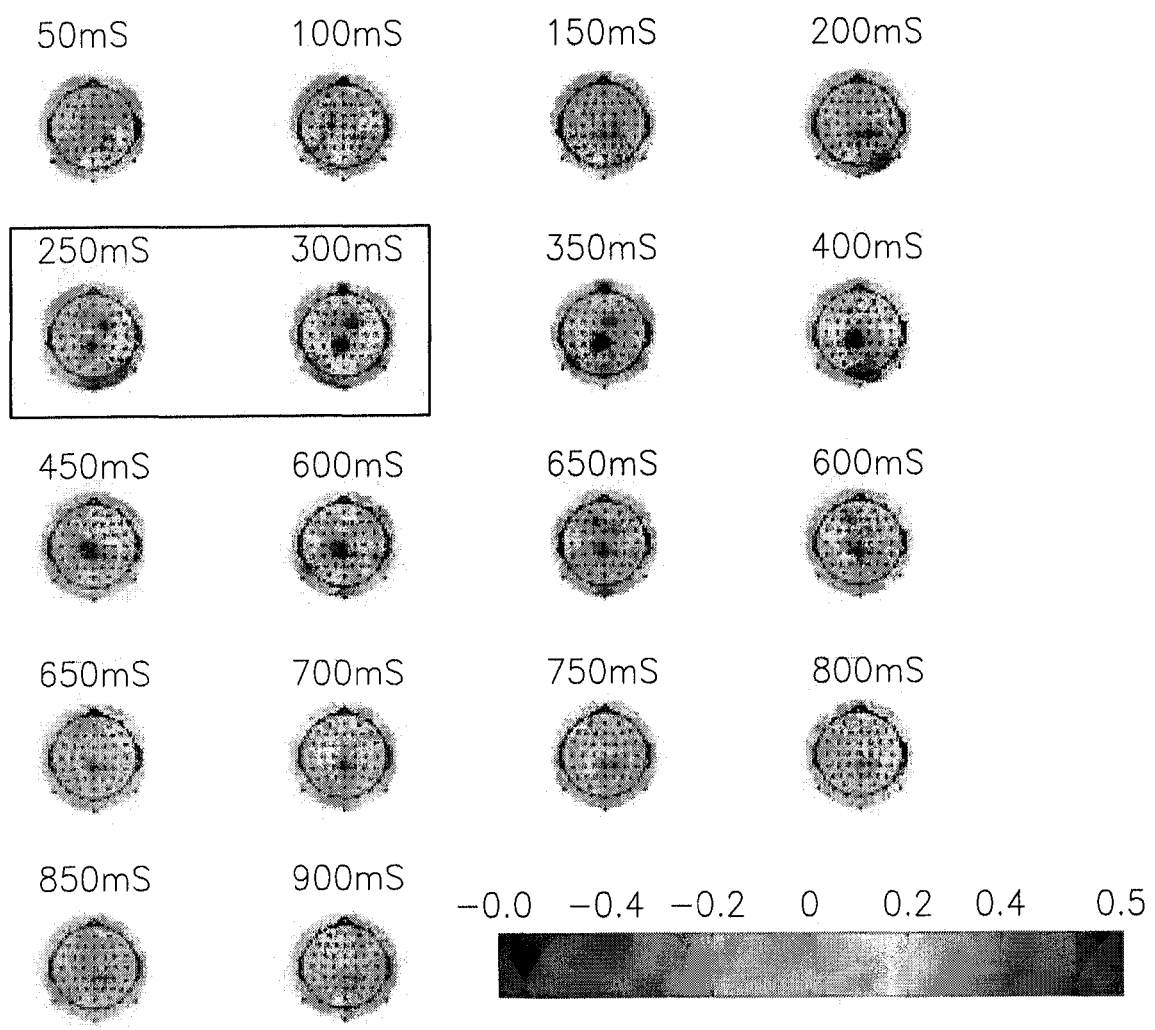

The nature of the SWFP algorithm allows also to investigate the spatial topography of Standard/Targets discriminating brain patterns, as depicted by the discriminating weights at each scalp location. As described above, the spatial distribution of discriminating weights at time t is given by U(t). FIG. 5 depicts, for a sample subject, the mean spatial topography of Target/Standard discrimination weights, averaged over all cross validation permutations, at different time points post stimulus presentation. It is clear that discriminating weights build up towards '"300 ms post-stimulus presentation, and that for this subject they are maximal around CPz, in the central-parietal area.

Figure 6:
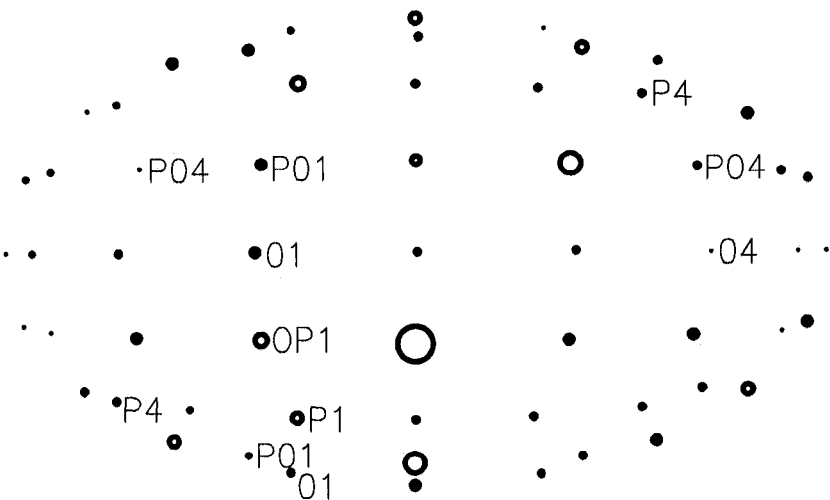

For further analysis we therefore investigate the corresponding mean spatial distribution of discriminating activity, averaged over all cross validation permutations, at the subject's best latency as depicted in FIG. 6. Since best latencies vary at different cross validation permutations we refer to the median of the evaluated probability distribution of best latencies, as the best latency of discrimination of each subject, denoted by $d_{best}$.

Figure 7:
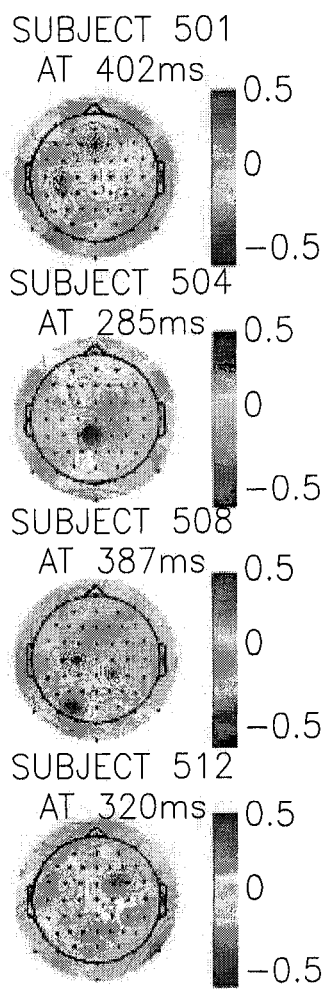
Figure 7:
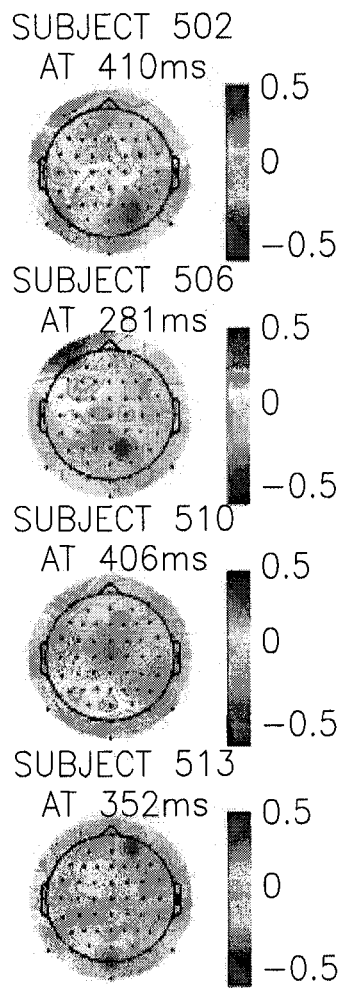
Figure 7:
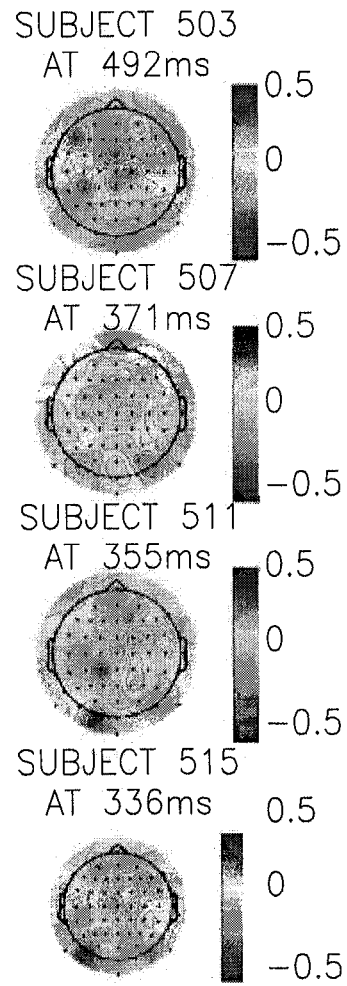

FIG. 7 summarizes the spatial distribution of discriminative activity for all subjects, each at their best latency for discrimination (U(~best)). While peak discriminate activity at best latencies tend to be at central, parietal or occipital electrodes, the exact location of the most discriminative activity is subject specific. In few subjects discriminative activity was found to be less localized and to involve also frontal regions. In the specific experiment considered here, the same image exemplar could appear in different blocks as either a Target/Standard stimulus (e.g face images were "Targets" in a Face-Target block, and "Standards" in all other blocks). Testing was thus performed separately for the image-Target blocks and image-Standard blocks. Performance was computed for each image exemplar, and averaged over all presented image exemplars in the experiment. We found that this leave-one-out voting procedure for repetitions of each image exemplar, dramatically improves image classification performance by an average of 16.5% correct classification (12.5-20% for different subjects), to near perfect classification in some subjects (83-95.5%; mean 89.4%). Specifically, it increases Target-hit rates by an average of 20% (17-27% for different subjects), and reduces false-alarms by an average of 22% (16-25% for the different subjects), resulting in hit rates of 7591% (mean 83% hits) and false alarm rates approaching zero (0-9%; mean 4%).

Despite considerable advances in computer vision, the capabilities of the human visu-perceptual system still surpasses even the best artificial intelligence systems, especially as far as its flexibility, learning capacity, and robustness to variable viewing conditions. Yet when it comes to sorting through large volumes of images, such as micro- and macroscopic medical images, or satellite aerials, human are generally accurate, but too slow. The bottleneck does not stem mainly from perceptual processes, which are pretty quick, but from the time it takes to register the decision, be it orally, in writing, or by a button press. To overcome this impediment, observers can be freed from the need to overtly report their decision, while a computerized algorithm sorts the pattern of their single trial brain responses, as images are presented at a very high rate.

Since EEG is characterized by a low signal to noise ratio (SNR), it is traditionally analyzed by averaging out the noise over many repetitions of the same stimulus presentation. However, for the purpose of using EEG to label single images in real time (or nearly so), the algorithm must be able to deal with single trials. This was complicated in the present implementation by the need to present the images rapidly (at 10 Hz), such that brain responses to subsequent image presentations overlapped. That is, the response to an image presentation has not yet decayed before the next stimulus was presented. This requires special consideration when selecting a classification algorithm.

In fact, the inventors have discovered that the PCA, implemented in both SWFP and HDPCA on time series from individual channels, performs a kind of spectral decomposition, where the first few principle components turn out to represent the lowest frequency components of the original signal. Noise reduction is thus an outcome of choosing the first few principal components, or rather a combination of the lowest frequency components, explaining the original variability in the signal.

The main difference of SWFP from the other two algorithms (HDCA and HDPCA) relies mainly in the details of the spatial information in use. All three algorithms start with a first step of linear classification, which is used to determine the discrimination-based spatial projection of the data.

Moreover, SWFP amplifies the original data matrix by the spatio-temporal discriminating weights prior to PCA suggesting it as a feasible algorithm to be used in the future for automatically exploring spatio-temporal activations at the basis of other discriminating tasks. Interestingly, we found variance across subjects in the exact time and location of the most discriminative activity, indicating individual differences. For example, in a few of the subjects discriminative activity was found to be less localized and to involve also frontal scalp regions contributing to Target/Standard discrimination. While the pattern of discriminating activity in some subjects differs from the classical spatio-temporal distribution of P300 ERPs, we find the patterns to be reliable and informative across trials; in fact, some subjects with non-classical spatiotemporal distribution of discriminating weights, show the highest single trial classification performance. This suggests that the spatio-temporal brain representation of Target detection is subject-specific, yet for each subject it is consistent across trials.

As will be appreciated by one skilled in the art, aspects of the present invention may be embodied as a system, method or an apparatus. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The aforementioned flowchart and block diagrams illustrate the architecture, functionality, and operation of possible implementations of systems and methods according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions. In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment. Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention.

The invention claimed is:

1. A method for conducting a single trial classification of Electroencephalography (EEG) signals of a human subject, the method comprising:

displaying to the subject a series of images containing target images and non-target images, wherein at least some of the target images are repeated in said series;

by a set of EEG sensors, acquiring said EEG signals;

by a special purpose computer processor, receiving said EEG signals from said EEG sensors and processing said EEG signals to provide a spatio-temporal representation comprising time points and respective spatial distribution of said EEG signals;

by said special purpose computer processor, classifying said time points independently, using a linear discriminant classifier, to compute spatio-temporal discriminating weights;

by said special purpose computer processor, using said spatio-temporal discriminating weights to amplify said spatio-temporal representation by said spatio-temporal discriminating weights at spatio-temporal points respectively, to create a spatially-weighted representation, and storing said spatially-weighted representation in a memory;

by said special purpose computer processor, using Principal Component Analysis (PCA) in a temporal domain for dimensionality reduction, separately for each spatial channel of said EEG signals, to create a PCA projection, and storing said PCA projection in a memory;

by said special purpose computer processor, retrieving said spatially-weighted representation and said PCA projection from said memory and applying said PCA projection to said spatially-weighted representation onto a plurality of principal components, to create a temporally approximated spatially weighted representation containing for each spatial channel, PCA coefficients for said plurality of principal components; and by said special purpose computer processor, classifying said temporally approximated spatially weighted representation, over said spatial channels of said EEG signals, using said linear discriminant classifier, to output a label classifying each image of the images series as belonging to either said target image or to said non-target image.

2. The method according to claim 1, wherein said linear discriminant classifier is a Fisher Linear Discriminant (FLD) classifier.

3. The method according to claim 1, wherein said spatio-temporal representation comprises a data matrix X whose columns represent time points, each time point being spatial distribution of the EEG signals at time t, wherein said spatio-temporal discriminating weights comprises matrix U, wherein said spatially-weighted representation comprises matrix $X_w$, wherein said PCA projection comprises matrix A, wherein said plurality of principal components comprise first K principal components, wherein said temporally approximated spatially weighted representation comprises matrix $\hat{X}$ of size D×K, wherein D is a number of the EEG spatial channels, and wherein said output labels are represented by $y_n$ such that: $y_n = f(\hat{X}_n)$; wherein $\hat{X}_n = A*X_w$, $X_w = U.*X^T_n$, and $\hat{X}_n = A(U.*X^T_n)$.

4. The method according to claim 1, wherein the images of the image series are presented to the human subject at a rate of 10 Hz.

5. The method according to claim 1, wherein the target images are related to a class including different images of similar objects.

6. The method according to claim 1, wherein the human subject is provided with a priori knowledge regarding said target images, and wherein said labels are output based on said a priori knowledge.

7. The method according to claim 1, wherein the human subject lacks any a priori knowledge regarding said target images, and wherein said labels are output based on said lack of a priori knowledge.

8. The method according to claim 1, wherein the method is implemented within a brain computer interface.

9. A system for conducting a single trial classification of Electroencephalography (EEG) signals of a human subject generated responsive to a series of images containing target images and non-target images, the system comprising:

EEG sensors and samplers configured to obtaining said EEG signals; and a computer processor configured to:

receive said EEG signals from said EEG sensors;

process said EEG signals to provide a spatio-temporal representation comprising time points and respective spatial distribution of said EEG signals;

classify said time points independently, using a linear discriminant classifier, to compute spatio-temporal discriminating weights;

use said spatio-temporal discriminating weights to amplify said spatio-temporal representation by said spatio-temporal discriminating weights at said time points respectively, to create a spatially-weighted representation, and store said spatially-weighted representation in a memory;

use Principal Component Analysis (PCA) in a temporal domain for dimensionality reduction, separately for each spatial channel of said EEG signals, to create a PCA projection, and store said PCA projection in a memory;

retrieve said spatially-weighted representation and said PCA projection from said memory and apply said PCA projection to said spatially-weighted representation onto a plurality of principal components, to create a temporally approximated spatially weighted representation containing for each spatial channel, PCA coefficients for said plurality of principal components; and classify said temporally approximated spatially weighted representation, over said spatial channels of said EEG signals, using said linear discriminant classifier, to output a label classifying each image of the images series as belonging to either the target image or the non-target image.

10. The system according to claim 9, wherein said linear discriminant classifier is a Fisher Linear Discriminant (FLD) classifier.

11. The system according to claim 9, wherein said spatio-temporal representation comprises a data matrix X whose columns represent time points, each time point being spatial distribution of the EEG signals at time t, wherein said spatio-temporal discriminating weights comprises matrix U, wherein said spatially-weighted representation comprises matrix $X_w$, wherein said PCA projection comprises matrix A, wherein said plurality of principal components comprise first K principal components, wherein said temporally approximated spatially weighted representation comprises matrix $\hat{X}$ of size D×K, wherein D is a number of the EEG spatial channels, and wherein said binary decisions series is output labels are represented by $y_n$ such that:

$y_n = f(\hat{X}_n)$; wherein $\hat{X}_n = A*X_w$, $X_w = U.*X^T_n$, and $\hat{X}_n = A(U.*X^T_n)$.

12. The system according to claim 9, wherein the system is implemented within a brain computer interface.

* * * * *